(12) United States Patent
Mach et al.

(10) Patent No.: US 8,852,231 B2
(45) Date of Patent: Oct. 7, 2014

(54) FLUID APPLICATOR

(71) Applicant: Bergen Medical Industries Corporation, Cedar Knolls, NJ (US)

(72) Inventors: Hung Mach, Flushing, NY (US); Richard Costa, Bedminster, NJ (US); Mitchell Tung, Basking Ridge, NJ (US)

(73) Assignee: Bergen Medical Products, Inc., Cedar Knolls, NJ (US)

( * ) Notice: Subject to any disclaimer, the term of this patent is extended or adjusted under 35 U.S.C. 154(b) by 141 days.

(21) Appl. No.: 13/633,243

(22) Filed: Oct. 2, 2012

(65) Prior Publication Data

US 2014/0094847 A1 Apr. 3, 2014

(51) Int. Cl.
*A61B 17/08* (2006.01)

(52) U.S. Cl.
USPC .......................................... 606/214; 401/132

(58) Field of Classification Search
CPC ................... A61B 17/03; A61B 17/06; A61B 2017/00445
USPC ......... 606/151, 212, 214; 604/3, 96; 401/132, 401/133
See application file for complete search history.

(56) References Cited

U.S. PATENT DOCUMENTS 8,550,737 B2 * 10/2013 Ruiz et al. .................... 401/134
2012/0070220 A1 3/2012 Ruiz, Sr. et al.

* cited by examiner

*Primary Examiner* — Victor Nguyen
(74) *Attorney, Agent, or Firm* — Mitchell J. Mehlman, Esq

(57) ABSTRACT

Fluid applicators utilizing a cutter and an ampule containing fluids, such as topical adhesives, and methods for safe, sterile, one-time use of fluid applicators for expressing fluids, such as wound sealing adhesives, are provided.

8 Claims, 2 Drawing Sheets

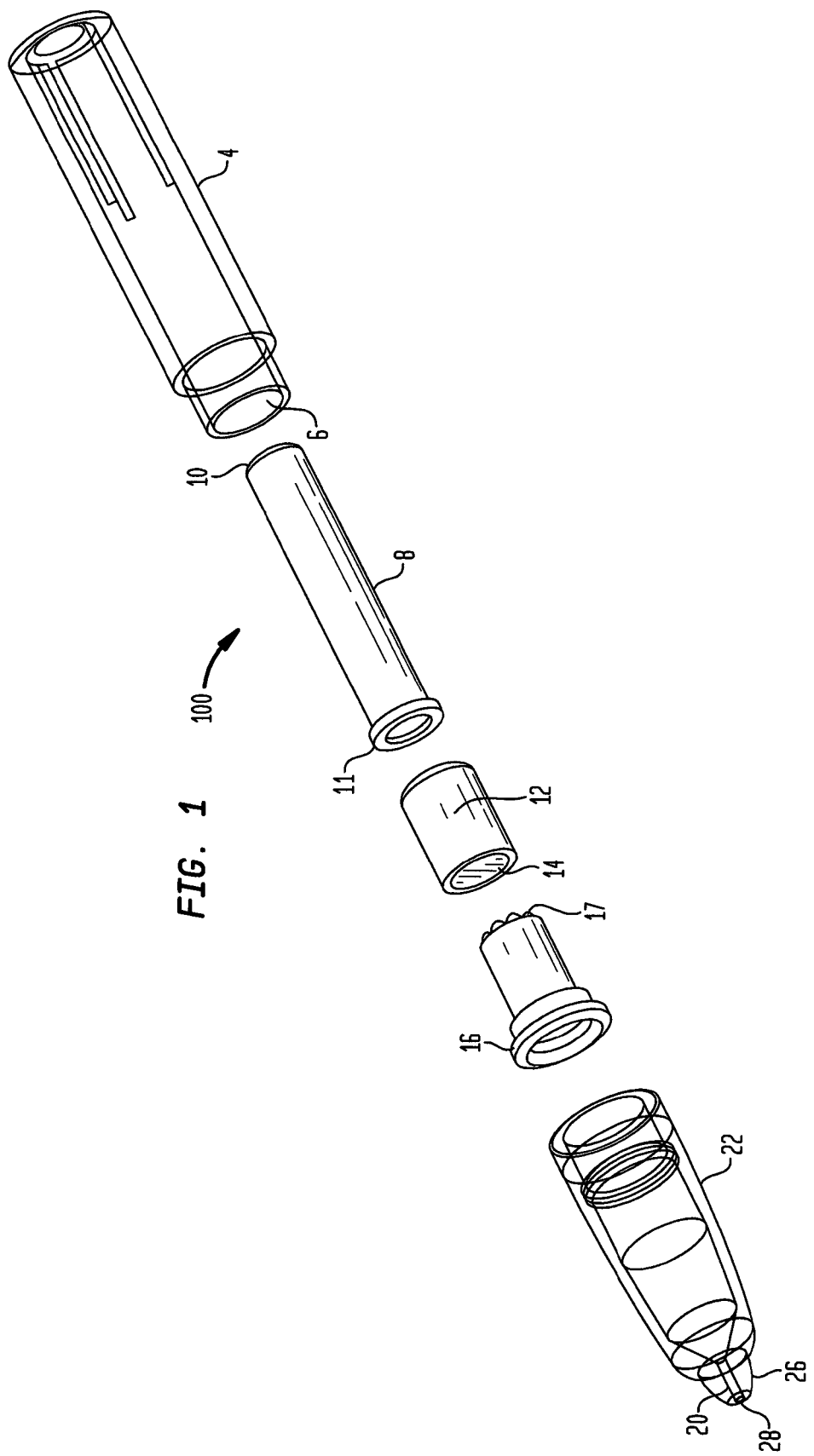

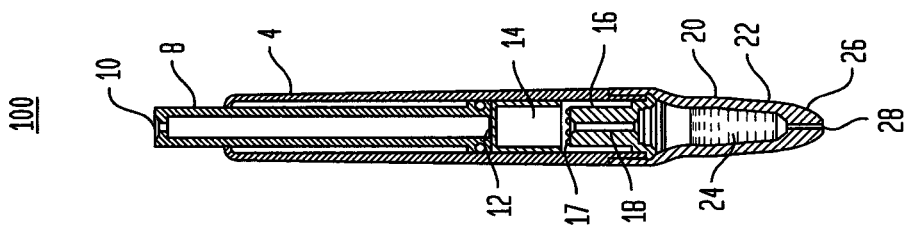
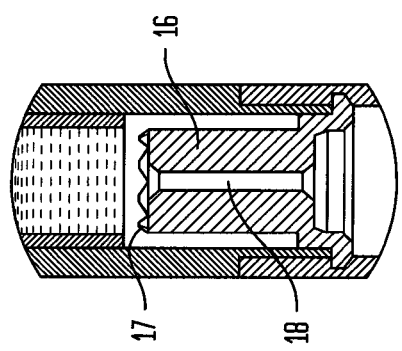
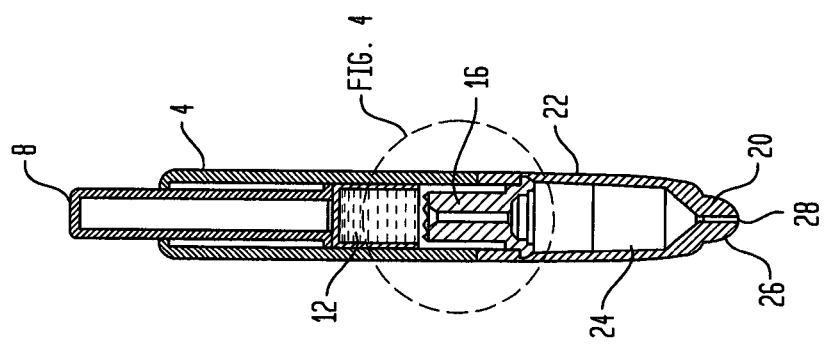
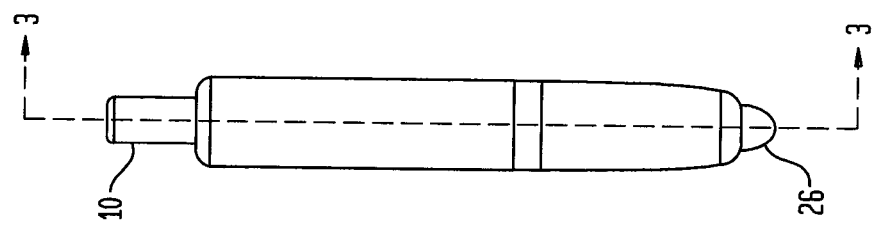

FLUID APPLICATOR

BACKGROUND OF THE INVENTION

The present invention relates to fluid application devices and methods of using such devices.

Many people, including doctors and nurses require applicators for applying fluids such as, for example, topical skin adhesives. Various adhesive materials including cyanoacrylates can be used for closing or protecting wounds to the skin caused by trauma or surgery.

Emergency rooms, surgical suites, and many other health care settings find that topical skin adhesives are a safe and effective way to close wounds and prevent infection. Use of skin adhesives can also help reduce the pain and the fear that may accompany stitching the wound closed.

The original cyanoacrylate adhesives were discovered in 1942 in a search for materials to make clear plastic gun sights for the war. However, cyanoacrylates were quickly rejected by researchers because they stuck to everything. In 1951, cyanoacrylates were rediscovered by Eastman Kodak researchers, who recognized their true commercial potential.

The idea of using "super glue" to close wounds has been popular since the Vietnam War, when it was reportedly used in battlefield triage to raise the survival rate of American soldiers. Cyanoacrylate adhesives were reportedly used in veterinary use for mending bone, hide, and tortoise shell by about the early 1970s. Butyl cyanoacrylate has been used medically since the 1970s, but, due to its potential to irritate the skin, the U.S. Food and Drug Administration (FDA) did not approve its use as a medical adhesive until 1998.

Research has demonstrated the use of cyanoacrylate in wound closure as being safer than traditional suturing. Adhesives have demonstrated better performance in the time required to close a wound, incidence of infection, and cosmetic appearance.

This adhesive would closure technology as grown into a multi-million dollar business and is now widely accepted by the FDA and the worldwide medical community.

While standard "superglue" is typically ethyl cyanoacrylate (ECA), many custom formulations have come to be used for specific applications. Variations on N-butyl-cyanoacrylate are used for medical applications.

For example, Dermabond® is a Johnson and Johnson product that was first released in January 1998. It was the first surgical skin adhesive approved in the United States. Dermabond® has a purple tint that allows the health care professional to see where it is applied. It comes in a single-use applicator. According to Ethicon, a division of Johnson and Johnson, Dermabond® is recommended for facial wounds and surgeries because it does not leave scarring like sutures.

LiquiBand® Surgical skin adhesive was first marketed in the United Kingdom, and became available in the United States in 2009. Liquiband® comes in single-use containers. Liquiband® comes in seven different types of applicators. Each applicator is designed for a specific set of use circumstances and conditions. These include applicators for use in general surgery, laparoscopic surgeries, lacerations and minor wounds.

Histoacryl® topical skin adhesive is marketed by Aesculap. Their marketing material claim that it bonds in seconds. Histoacryl® comes in a clear or blue tint. Hystoacryl® is available in single use applicators.

According to Tissue Seal's website, Histoacryl does not contain stabilizers, and thus is stronger and needs fewer applications than similar products. The manufacturer also says that this difference keeps the applicators from clogging or drying out. The formula dries when it comes into contact with water or water-containing tissues like skin. Hystoacryl® was created and first marketed in Germany in 1968.

Indermil® tissue adhesive was approved in September 2002 for use in closing incisions and lacerations. The product is recommended for use in closing laparoscopic incisions. Indermil® is marketed by United States in single-use applicators.

Nexaband® is a veterinarian grade of Dermabond®. It is used in veterinarian clinics to close wounds on cats and dogs. Nexaband® is colorless and recommended specifically for cat declawing procedures. It is marketed by Abbott Animal Health and is not appropriate for use on people.

Applicators for the application of fluid, and in particular, adhesives to wound, require ergonomic designs that are easy to operate. It is advantageous for such applicators to include indicia for quick identification of a new applicator, rather than a used applicator.

The use of fluid or adhesive applicators allows a user, such as a surgeon or other medical professional, to control the application of fluid to a wound. It is desirable to allow the user to apply coating of desired thicknesses, widths, and lengths to a wound or other area that requires treatment.

Non-compliance with a prescribed regimen of treatment can result wound dehiscence, a surgical complication in which a wound breaks open along surgical suture, infection, additional surgery, pain and suffering for the patient, and unnecessary health care costs.

Known applicators include configurations in which a glass ampule is cracked by the hand action of a user to release a fluid. In some applicators, the fluid is contained in an aluminum foil tube. Other applicators can include a process in which a glass ampule is cracked using a gull wing hammer to release fluid or where a sponge is used to contain and express a fluid.

Known applicators have severe limitations. One such limitation is the inability of a user to express fluid, an adhesive for example, onto a wound in a precise and controlled manner. Another such limitation is the inability of a user to readily determine that the device has been used and needs to be replaced.

There are numerous other limitations of the existing technology which will become apparent with respect to the present disclosure. For example, aluminum foil applicators do not allow a user to see how much adhesive is remaining in the applicator, thus creating the potential risk of a surgeon running out of adhesive before the wound is completely closed.

"Single body" applicators designs are limited in that the applicators are pressurized when filling, thus when the tip is removed, the pressure inside the applicator may cause fluid to leak out or cause the user to apply more adhesive than intended (i.e. because pressure inside forces the fluid out of the applicator tip). Further limitations of some applicator designs include having to remove a tip to open the applicator in a sterile operating room environment. As such, the tip needs to be tracked and inventoried to ensure it has not been left in the patient, potentially causing life threatening complications. In addition, a narrow tip only allows for a "spot wielding" application technique which is time consuming and inefficient. Furthermore, with narrow tips, there is a risk that fluids, such as wound sealing adhesives, may enter the wound inadvertently.

Further applicator design limitations include the crushing of a glass ampule to activate and release an adhesive formulation. Such crushing of a glass ampule may cause shards of glass to penetrate a protective covering, if any, thereby jabbing the user's had, such as a surgeon or a doctor, with glass. While some designs have taken steps to limit glass shard penetration, this risk has not been eliminated. For example, for the last twelve years, hospitals have reported glass shard penetrations that have caused damage to surgeon's hands to the FDA Manufacturer and User Facility Device Experience (MAUDE) for adverse event reporting.

In addition, the ability to easily express and control the application of fluid with the aforementioned devices is difficult since the user, such as a surgeon or doctor, needs to control the expression of adhesive through multiple layers of a protective cover and the crushed ampule.

Some known applicator designs require a tab to be folded back to activate the applicator so that a fluid formulation can be released. Such designs are limited in that they require that the applicator tip, which can be a foam tip, come in contact with the wound. The FDA warns against such contacts. In addition, when an applicator having a foam tip comes in contact with body fluids, such fluids can be comingled with the applicator fluid, thus cause performance degradation. In some designs, the edges created by folding back a tab are sharp and have been known to cut or scrape patients or users of such applicators.

As detailed below, the present invention solves these and other difficult problems in a novel manner by improving the overall ease of compliance with a wound sealing protocols. For example, the instant invention is more efficient because a fresh new unit is easily identified for each application and the expression of fluid, such as adhesive, can be easily and carefully controlled by a user. The instant invention also eliminates the possibility that a user is cut by glass shards from an ampule.

Fluid applicators comprising novel multifunctional cutters and channels for opening fluid containing ampules, and expressing fluids, are disclosed herein.

SUMMARY OF THE INVENTION

In one aspect of the present invention an apparatus comprises a case. The case includes an aperture. A plunger can be disposed within the case. The plunger has a first end and a second end. The plunger has a first undispensed position and a second dispensed position. A puncture cap has a cutter and a channel. The puncture cap can be disposed within the case. A sealed ampule contains a fluid. The ampule can be disposed within the case. A bulb has a storage reservoir and an aperture. The bulb can be connected to the case and the puncture cap. The bulb can receive the fluid through the channel and a user can express the fluid through the aperture in the bulb.

In some embodiments, the bulb is comprised of a translucent or a transparent material.

In other embodiments, the bulb has a rounded tip.

In some embodiments, the cutter has at least two cutting blades.

In other embodiments, the channel is a tube.

In yet other embodiments, the tube is disposed in a central region of the puncture cap.

In certain embodiments, the ampule is comprised of a glass body and a foil lid.

In certain other embodiments, the ampule is comprised of a polymeric body and a foil lid.

In another aspect of the invention, a method comprises the steps of depressing a plunger thereby forcing a puncture cap having one or more teeth against a sealed ampule containing a fluid; puncturing the sealed ampule; forcing the fluid through a channel in the puncture cap and into a bulb; accumulating the fluid in the bulb; and expressing the fluid through an aperture in said bulb.

In some embodiments of this aspect, the ampule comprises a glass body and a foil seal.

In still other embodiments, the bulb includes a rounded tip.

In one embodiment of this aspect, the method further includes the step of forming a wound cover using the fluid.

Another embodiment comprises the step of forming a film with the rounded tip.

In certain embodiments, the fluid comprises a cyanoacrylate adhesive.

In some embodiments the method further comprises the step of covering a wound thereby forming a sterile wound cover.

In certain other embodiments, the method further comprises the step of expressing the fluid and forming more than one layer.

In yet another aspect of the invention, an apparatus comprises a case having an aperture. A plunger is disposed slidably and telescopically within the case. An ampule contains a fluid. A cutter is disposed to cut the ampule when a user applies pressure to the plunger. A bulb includes a reservoir. The bulb receives substantially all of the fluid from the ampule when a user applies pressure to the plunger.

In some embodiments of this aspect, the fluid has a volume of between about 3.0 milliliters (ml) and about 0.3 milliliters (ml).

In certain embodiments, the fluid has a volume of about 0.7 milliliters (ml).

In some embodiments, the bulb is transparent or translucent.

In some embodiments, a non-glass ampule can contain a fluid formulation; the ampule provides a sterile environment for the fluid, including odor, color or chemicals contamination.

In some embodiments, the applicator works in conjunction with a target formulation; the formulations have a plurality of viscosities and polymerization times. For example, the viscosity can be between about 1 cps and 1000 cps; preferably between about 75 cps to about 150 cps.

The drying or curing time of the adhesive can be between about 5 seconds and 5 minutes, preferably between about 90 seconds and about 3 minutes.

Certain embodiments require that the applicator is compatible with either gamma or gas sterilization methods known in the industry.

Some embodiments provide product stability for a at least two years of shelf life thus preserving sterility and usability of the fluid formulation with little or no discoloration and minimal deterioration.

Certain embodiments of the applicator provide for visual observation of the fluid or formulation.

Other embodiments of the applicator allow a user to control flow of a fluid formulation by applying force to the device; this expression force can be modified such that a user can apply the force with ease and comfort.

In certain embodiments, the expression of a fluid formulation does not produce bubbles or gaps in the applications film or fluid.

In some embodiments, the applicator's tip can be smooth; the tip can be angled or can be rounded to provide smooth application of a fluid over a wound Some embodiments of the applicator can hold 0.7 ml of fluid; volumes of between about 0.35 ml and about 1.5 ml can be used for smaller and longer incisions.

In some embodiments, a 0.7 ml volume can cover an incision about 15 cm in length. Film thickness can be between about 0.5 mm to about 5.0 mm; preferably about 2.0 mm in thickness.

Other embodiments of the applicator should be able to provide for fine and wide lines. With of the lines can be in the range of about 0.010" to about 0.25".

BRIEF DESCRIPTION OF THE DRAWINGS

FIG. 1 is an isometric exploded view of a fluid applicator according to one embodiment of the present invention.

FIG. 2 is a plan view of some of the elements included in the fluid applicator of FIG. 1.

FIG. 3 is cross-sectional view of the fluid applicator as indicated by arrow 3 of FIG. 2.

FIG. 4 is a cross-sectional detail view of some of the elements included in the fluid applicator as indicated in FIG. 3.

FIG. 5 is another cross-sectional view of some of the elements included in the fluid applicator of FIG. 1.

DETAILED DESCRIPTION

As used herein, the terms fluid or fluids refer to any a substance, as a liquid or gas, that is capable of flowing and that changes its shape at a steady rate when acted upon by a force tending to change its shape. The terms fluid and fluid may also include delivery forms typically used for topical administration, such as encapsulated and packaged liquid suspensions or emulsions, powders, creams, salves, serums, ointments and the like. The terms fluid, adhesive, medicine or medication may be singular or plural and are used interchangeably herein.

As used herein, the terms fluid, medicine and or medication refer to prescription and over-the-counter medications, dietary supplements such as vitamins, minerals or cosmetic products. Further, the terms fluid, medicine and or medication refer to any product contained in an ampule form which the user has a need or desire to use in a user controlled application.

As used herein, an ampule or ampoule or phial is defined as a sealed vial made of glass, plastic or other material that contains a fluid, such as and adhesive or a sterile medicinal solution or a powder to be made into a solution for subcutaneous, intramuscular, or intravenous injection. An ampule can be a small, hermetically sealed flask or container made of glass or polyethylene, e.g., one containing adhesive for topical administration.

One embodiment of the present invention is the ACTA-BOND™ topical skin adhesive applicator. The applicator is designed to store and easily express topical skin adhesive formulations used for the closure of surgical wounds from incisions or lacerations caused from trauma. In this embodiment, the applicator is a single use applicator that is ergonomically designed for human factors. Such factors allow a surgeon or medical professional to control the application of adhesive, as well as varying amounts of formulation to be expressed for creating thin or narrow applications.

As shown in FIGS. 1-5, one non-limiting embodiment of the applicator 100 includes a cover 4. The cover includes an aperture 6 such that a plunger 8 can be fitted telescopically within the aperture.

Plunger 8 has a cylindrical body comprising a first end 10 and a second end 11. The first end 10 of the plunger can be easily depressed with for example, thumb pressure to allow the plunger to slide within the cover 4.

Ampule 12 is housed within the cover 4 in a collinear arrangement with the longitudinal axis of the plunger 8 and the device 100. The second end 11 of the plunger 8 is disposed such that force applied to the first end of the plunger will result in application of the force from the second end of the plunger 8 to the ampule 12.

The ampule 12 is filled with a fluid (not shown) and includes a foil lid 14 to store a fluid, such as an adhesive formulation. Thus, the ampule 12 is in proximity to the second end 11 of the plunger.

The cap 16 includes a cutter 17 and an internal channel or cannula 18. The cap is aligned to be collinear with the foil lid 14 of the ampule 12.

Bulb 20 includes a wall 22, a reservoir 24 and an expression tip 26 having an aperture 28. The bulb is used to store released fluid and for expression of a fluid out of the device 100 and, for example, onto a wound.

The abovementioned components, as shown in FIGS. 1-5, can be arranged such that they can telescope into an easy assembled fluid applicator 100. The user receives the applicator 100 with the plunger 8 in the "ready" position. By using the same thumb or finger action as clicking a pen, the user presses down on the first end of plunger 8 to activate the applicator. The plunger slides with respect to the cover 4 such that the second end of the plunger forces the foil lid 14 of the ampule 12 against the cutter 17. The plunger 8 is then flush with the cover 4, thus indicating the device has been activated. In this way, a user can easily see that the device is active thus eliminating the risk for reuse which can be unsafe to a patient or recipient of the fluid.

The pressure generated from the plunger 8 forces the ampule 12 against the cutter 17, and causes the cutter 17 to cut the foil lid 14 of the ampule 12 and allows the fluid formulation to travel through the channel 18 into the reservoir 24.

As described above, a user can use a motion similar to that of activating a pen, that is, a thumb or finger motion that causes the plunger to move from a first undispensed position to a second dispensed position. In addition to the configuration shown in FIGS. 3-4, the cutter can be made in a plurality of configurations including one or more cutting blades, or edges or protrusions, such that pressure on the plunger 8 causes the cutter 17 to penetrate or puncture the ampule cover. Further, the ampule lid or cover 14 may be foil or any other material that can be punctured by a cutter.

When the cutter punctures the sealed ampule, the fluid in the ampule flows through the puncture cap. As shown in FIG. 4, the cap 16 includes a channel 18 in the form of a tube having a circular cross-section.

Other configurations, such as a cup having two or more channels may be utilized in the present invention. The number and geometry of the channels can be adjusted, depending on, for example, the viscosity of the fluid, to allow fluid to flow from a first storage area, such as an ampule, to a usage area, such as a reservoir.

The bulb 20 accumulates the fluid that is forced from the ampule 12 into the reservoir 24. A user can apply a plurality of pressures to the fluid in the reservoir by squeezing the bulb, thus expressing the fluid or fluid formulation out of the aperture 28 of the bulb. By using a plurality of pressures and holding the applicator at different distances from the wound or other area requiring treatment, a user can determine the size and length of the fluid applied. In addition, a user can utilize the curved tip 30 of the bulb to smooth or apply the expressed fluid formulation as needed.

The components of the applicator can be molded or fabricated from any suitable durable structural material, for example, a polymeric material or combination of polymers, or metallic materials, or ceramic material, or combinations thereof. Suitable materials and manufacturing methods will be well known to those skilled in the art of packaging or medical devices. Most of the components can be manufactured using injection molding or any other suitable polymer processing method or combination of methods.

A plurality of applicator geometries, cutter configurations, and bulb configurations are contemplated within the scope of the present invention. Nothing in this disclosure is intended to limit the size of the applicator.

Although the invention herein has been described with reference to particular embodiments, it is to be understood that these embodiments are merely illustrative embodiments and that other arrangements may be devised without departing from the spirit and scope of the present invention as defined by the disclosure herein.

What is claimed is:

1. An apparatus comprising:
    (a) a case, said case including an aperture;
    (b) a plunger, said plunger being disposed within said case, said plunger having a first end and a second end, said plunger having a first undispensed position and a second dispensed position;
    (c) a puncture cap, said puncture cap having a cutter and a channel, said puncture cap being disposed within said case, said cutter having at least two cutting blades;
    (d) a sealed ampule, said ampule containing a fluid, said ampule being disposed within said case; and
    (e) a bulb having a storage reservoir and an aperture, said bulb being comprised of a translucent or transparent material, said bulb having a curved or rounded tip, said bulb being connected to said case and said puncture cap wherein said bulb receives said fluid through said channel and a user can express said fluid through said aperture.

2. The apparatus of claim 1, wherein said channel is a tube.

3. The apparatus of claim 2, wherein tube is disposed in a central region of said puncture cap.

4. The apparatus of claim 1, wherein said ampule is comprised of a glass body and a foil lid.

5. The apparatus of claim 1, wherein said ampule is comprised of a polymeric body and a foil lid.

6. An apparatus comprising:
    (a) a case having an aperture;
    (b) a plunger, said plunger being disposed slidably and telescopically within said case;
    (c) an ampule, said ampule containing a fluid;
    (d) a cutter; said cutter having at least two cutting blades, said cutter being disposed to cut said ampule when a user applies pressure to said plunger; and
    (e) a bulb, said bulb including a reservoir, said bulb being comprised of a translucent or transparent material, said bulb having a curved or rounded tip, wherein said bulb receives substantially all of said fluid from said ampule when a user applies pressure to said plunger.

7. The apparatus of claim 6, wherein said fluid has a volume of between about 3.0 milliliters and about 0.3 milliliters.

8. The apparatus of claim 6, wherein said fluid has a volume of about 0.7 milliliters.

* * * * *